(12) United States Patent
Kim et al.

(10) Patent No.: US 9,814,726 B2
(45) Date of Patent: Nov. 14, 2017

(54) COMPOSITION FOR PREVENTING OR TREATING FATTY LIVER DISEASES

(71) Applicant: LG CHEM, LTD., Seoul (KR)

(72) Inventors: Soon Ha Kim, Daejeon (KR); Hyoung Jin Kim, Daejeon (KR); Heui Sul Park, Daejeon (KR); Seo Hyun Ahn, Daejeon (KR); Min Ho Shong, Daejeon (KR); Hyo Kyun Chung, Daejeon (KR)

(73) Assignee: LG CHEM, LTD., Seoul (KR)

(*) Notice: Subject to any disclaimer, the term of this patent is extended or adjusted under 35 U.S.C. 154(b) by 0 days.

(21) Appl. No.: 15/304,715

(22) PCT Filed: Apr. 17, 2015

(86) PCT No.: PCT/KR2015/003869
§ 371 (c)(1),
(2) Date: Oct. 17, 2016

(87) PCT Pub. No.: WO2015/160213
PCT Pub. Date: Oct. 22, 2015

(65) Prior Publication Data
US 2017/0035776 A1    Feb. 9, 2017

(30) Foreign Application Priority Data
Apr. 18, 2014 (KR) .................. 10-2014-0046904

(51) Int. Cl.
*A61K 31/541* (2006.01)
*A61K 31/517* (2006.01)
*A61K 31/5377* (2006.01)

(52) U.S. Cl.
CPC .......... *A61K 31/541* (2013.01); *A61K 31/517* (2013.01); *A61K 31/5377* (2013.01)

(58) Field of Classification Search
CPC .................................................. A61K 31/541
See application file for complete search history.

(56) References Cited

U.S. PATENT DOCUMENTS

| | | |
|---|---|---|
| 2014/0024618 A1 | 1/2014 | Kim et al. |
| 2015/0038500 A1 | 2/2015 | Kim et al. |

FOREIGN PATENT DOCUMENTS

| | | | |
|---|---|---|---|
| EP | 1 873 144 A1 | 1/2008 | |
| KR | 10-2009-0018593 A | 2/2009 | |
| KR | 20090018593 A * | 2/2009 | ........... C07D 413/04 |
| KR | 10-2013-0058608 A | 6/2013 | |
| KR | 10-2013-0087283 A | 8/2013 | |
| KR | 10-2013-0140402 A | 12/2013 | |

OTHER PUBLICATIONS

International Search Report for PCT/KR2015/003869 (PCT/ISA/210) mailed on Jun. 30, 2015.

* cited by examiner

*Primary Examiner* — Kahsay Habte
(74) *Attorney, Agent, or Firm* — Birch, Stewart, Kolasch & Birch, LLP

(57) ABSTRACT

The present invention relates to a pharmaceutical composition for preventing or treating fatty liver diseases, containing (tetrahydropyran-4-yl)-[2-phenyl-5-(1,1-dioxo-thiomorpholin-4-yl)methyl-1H-indol-7-yl]amine or a pharmaceutically acceptable salt thereof as active ingredients. (Tetrahydropyran-4-yl)-[2-phenyl-5-(1,1-dioxo-thiomorpholin-4-yl)methyl-1H-indol-7-yl]amine or a pharmaceutically acceptable salt thereof, according to the present invention, can effectively inhibit fatty liver, hepatitis and hepatic fibrosis and can be useful for preventing or treating NAFLD, and in particular, NASH.

2 Claims, 5 Drawing Sheets
(3 of 5 Drawing Sheet(s) Filed in Color)

A

B                    C

COMPOSITION FOR PREVENTING OR TREATING FATTY LIVER DISEASES

TECHNICAL FIELD

The present invention relates to a composition for the prevention or treatment of fatty liver disease, specifically non-alcoholic steatohepatitis, which comprises (tetrahydropyran-4-yl)-[2-phenyl-5-(1,1-dioxo-thiomorpholin-4-yl)methyl-1H-indol-7-yl]amine or a pharmaceutically acceptable salt thereof as an active ingredient.

BACKGROUND ART

All fatty liver diseases, including fatty liver that is similar to alcoholic liver disorder which occurs to non-drinkers, are referred to as non-alcoholic fatty liver disease (NAFLD). In NAFLD patients, fatty acid synthesis in the liver is always activated, and the activation of fatty acid synthesis is an important factor involved in fatty liver development which is caused by metabolic syndrome.

NAFLD is roughly categorized into two groups: simple fatty liver which is generally thought of as having a mild prognosis, and non-alcoholic steatohepatitis (NASH), which is thought of as having a poor prognosis since simple fatty liver is continuously accompanied by inflammation or fibrosis, and NASH is regarded as one of the severe types of NAFLD.

Up to now, the Two-Hit theory has been known as the main pathologic mechanism of the occurrence and development of NASH. The Two-Hit theory is that the First Hit, which means factors such as life habits or genetic factors, develops simple fatty liver, and then multiple factors such as oxidative stress or inflammatory cytokines mainly induced at the fatty liver state act as the Second Hit to aggravate simple fatty liver to the severe stage of NASH.

The treatment for metabolic syndrome—which is known as one of the factors associated with occurrence of NASH—is very important, and in view of this aspect, medicaments—which have inhibitory effect against the metabolic syndrome such as insulin resistance improving agent, antioxidant, hyperlipidemia treatment agent, liver protecting agent, and antagonist of angiotensin II receptor—were tried clinically.

However, little development has been made on medicaments with clinical evidence for the treatment of NASH until now. For example, pioglitazone—which is an insulin resistance improving agent—was very promising as a medicament for the treatment of NASH, but it did not show practical improving effects in the phase 3 clinical trial, and it failed to obviously meet the standards for treatment medication due to problems of side effects such as risk of fracture, weight gain, heart failure deterioration and crisis.

Therefore, there has been an urgent need for studies about the prevention or treatment of non-alcoholic steatohepatitis.

Meanwhile, (tetrahydropyran-4-yl)-[2-phenyl-5-(1,1-dioxo-thiomorpholin-4-yl)methyl-1H-indol-7-yl]amine is a cellular necrosis inhibitor which is specific for mitochondria, and shows effects on inhibiting cell death by toxins or stress, increasing viability of cells, and anti-oxidation and anti-inflammation at the same time.

In other words, although (tetrahydropyran-4-yl)-[2-phenyl-5-(1,1-dioxo-thiomorpholin-4-yl)methyl-1H-indol-7-yl]amine is known to be effective for various diseases related to cellular necrosis, there has been no disclosure related to the prevention and treatment of fatty liver disease and metabolic syndrome, and no study has been conducted on this issue.

The present inventors accomplished the present invention by discovering that the treatment of the NASH animal model with (tetrahydropyran-4-yl)-[2-phenyl-5-(1,1-dioxo-thiomorpholin-4-yl)methyl-1H-indol-7-yl]amine effectively improves fatty liver, liver inflammation and liver fibrosis—which are the main pathological forms of NASH.

DISCLOSURE OF INVENTION

Technical Problem

The object of the present invention is the provision of a pharmaceutical composition for the prevention or treatment of fatty liver disease, which comprises (tetrahydropyran-4-yl)-[2-phenyl-5-(1,1-dioxo-thiomorpholin-4-yl)methyl-1H-indol-7-yl]amine or a pharmaceutically acceptable salt thereof as an active ingredient, in respect to NAFLD, specifically NASH.

Solution to Problem

To accomplish the object, the present invention provides a pharmaceutical composition for the prevention or treatment of fatty liver disease, which comprises (tetrahydropyran-4-yl)-[2-phenyl-5-(1,1-dioxo-thiomorpholin-4-yl) methyl-1H-indol-7-yl]amine or a pharmaceutically acceptable salt thereof as an active ingredient.

Herein, fatty liver diseases may be non-alcoholic fatty liver diseases, specifically non-alcoholic steatohepatitis or simple fatty liver, and the composition according to the present invention inhibits the accumulation of liver fat, and has effects on inhibiting inflammation and fibrosis of the liver by inhibiting oxidative stress or inflammatory cytokines derived from fatty liver.

Hereinafter, the present invention is described in more detail.

The agent for the prevention or treatment of fatty liver diseases according to the present invention comprises (tetrahydropyran-4-yl)-[2-phenyl-5-(1,1-dioxo-thiomorpholin-4-yl)methyl-1H-indol-7-yl]amine or a pharmaceutically acceptable salt thereof as an active ingredient.

In the present invention, ⌜fatty liver disease⌟ generally refer to disease in which disorder of the liver induced by deposition of neutral fat to hepatocytes, and includes alcoholic fatty liver disease and non-alcoholic fatty liver disease (NAFLD).

In the present invention, ⌜non-alcoholic fatty liver disease⌟ has the same meaning as non-alcoholic fatty liver and non-alcoholic fatty liver syndrome. Non-alcoholic fatty liver disease includes non-alcoholic steatohepatitis (NASH) and simple fatty liver.

Non-alcoholic fatty liver disease is, for example, a liver disorder which is characterized in macrovesicular liver fat deposition similar to alcoholic fatty liver disorder on the liver biopsy in spite that there is no history of apparent alcohol ingestion, and includes simple fatty liver with mild prognosis and progressive NASH. In addition, non-alcoholic fatty liver disease (NAFLD) has characteristics as below:

1. No apparent history of alcohol ingestion (amount of alcohol: 20 g or below/day).
2. Chronic liver disease—in which causes of diseases such as virus (HCV, HBV), autoimmune is obvious—is not counted.
3. Metabolic syndrome, obesity, diabetes, hyperlipidemia, hypertension, hyperuricemia, sleep apnea syndrome and the like are risk factors. In examples with multiple risk factors, the possibility of simple fatty liver and NASH increases.

4. Various diseases or medicaments which cause abnormality of lipid metabolism or mitochondria function are also included.

Non-alcoholic steatohepatitis (NASH) are, for example, defined as below:

1. Matteoni (Matteoni, C. A., et al., 1999, Gastroenterology, 116:1413-1419) classified NAFLD into 4 classes: class 1 means simple fatty liver, class 2 means steatohepatitis, class 3 means fatty liver necrosis (accompanying ballooning degeneration), and class 4 means liver cell necrosis which accompanies Mallory hyaline or fibrosis (accompanying ballooning degeneration). In view of the long term prognosis, types 3 and 4—which have significantly high frequency of progress to liver cirrhosis or liver related death—are considered as non-alcoholic steatohepatitis (NASH).

2. At Single Topic Conference 2002 of the American Association for the Study of Liver Diseases (Single Topic Conference 2002, Neuschwander-Tetri, B. A. et al., 2003. Hepatology, 37:1202-1219), class 3 and 4 NAFLD (Matteoni classification) are considered as NASH in view of steatosis (macrovesicular>microvesicular, accentuated in the central region of lobules), lobular inflammation (mild, infiltration of neutrophil or monocyte) and hepatocellular ballooning (apparent near steatotic liver cells, and in the central region of lobules) as the key histopathologic features of NASH.

3. Brunt (Brunt, E. M., et al., 1999, Am. J. Gastroenterol., 94: 2467-2474) classified the development progress of NASH into 4 stages according to the extent of fibrosis. Stage 1: central region of lobules (zone 3), Stage 2: 1+ portal area, Stage 3: bridging formation and Stage 4: liver cirrhosis.

In the present invention, ⌈simple fatty liver⌋ refers to a case in which only fat accumulation in liver cells is shown without accompanying necrosis, inflammation or fibrosis of liver cells, among lipoid liver diseases.

As a fatty liver disease to which an agent for prevention or treatment according to the present invention is applied, non-alcoholic fatty liver disease (NAFLD) is preferable, and simple fatty liver or non-alcoholic steatohepatitis (NASH) is more preferable.

As stated above, Two-Hit theory is largely supported as occurrence and development mechanism of NASH. Two-Hit theory is a hypothesis in which NASH progresses to another level by the occurrence and development mechanism below. First of all, as the First Hit, the accumulation of liver fat (fatty liver) occurs, and as the Second Hit, inflammation and fibrosis of the liver occur by oxidative stress or inflammatory cytokines derived from fatty liver.

About the First Hit, (tetrahydropyran-4-yl)-[2-phenyl-5-(1,1-dioxo-thiomorpholin-4-yl)methyl-1H-indol-7-yl]amine and a pharmaceutically acceptable salt thereof according to the present invention inhibits liver fat accumulation by inhibiting liver fat synthesis activation and content of liver triglyceride, thereby preferentially controlling fatty liver. In addition, about the Second Hit, the compound or a pharmaceutically acceptable salt thereof according to the present invention inhibits inflammation and fibrosis of the liver by inhibiting infiltration of lipid droplets and inflammatory cells in the liver, inhibiting oxidative stress and inflammatory cytokines, and inhibiting the expression of genes related to liver inflammation and genes related to liver fibrosis at the same time. By these action mechanisms, (tetrahydropyran-4-yl)-[2-phenyl-5-(1,1-dioxo-thiomorpholin-4-yl)methyl-1H-indol-7-yl]amine and a pharmaceutically acceptable salt thereof seems to have a high possibility of blocking the mechanism for occurrence and development of NASH effectively.

The agent for the prevention or treatment of fatty liver disease according to the present invention comprises (tetrahydropyran-4-yl)-[2-phenyl-5-(1,1-dioxo-thiomorpholin-4-yl)methyl-1H-indol-7-yl]amine or a pharmaceutically acceptable salt thereof, and pharmaceutically acceptable additives known in this field may be mixed if necessary. As additives that are optionally combinable, they may be changed in terms of dosage form or administration route, and include, for example, excipient, a binding agent, a disintegrating agent, a slip modifier, a flavor enhancer, a fragrance ingredient, a coloring agent or a sweetening agent.

Moreover, the agent for the prevention or treatment of fatty liver disease according to the present invention may be used in various forms of pharmaceutically acceptable formulations. As these forms, capsule, powder, tablet, fine granule, granule, injections, liquid, ointment or paste may be listed as preferable examples. Therefore, the agent for the prevention or treatment of fatty liver disease according to the present invention may be administered orally or parenterally to patients. Among them, oral preparation is preferred in view of its convenience for patients to use.

In the agent for prevention or treatment of fatty liver disease according to the present invention, the dosage of (tetrahydropyran-4-yl)-[2-phenyl-5-(1,1-dioxo-thiomorpholin-4-yl)methyl-1H-indol-7-yl]amine or a pharmaceutically acceptable salt thereof may be properly changed regarding the patient's situation such as age, weight, symptoms and administration route. For example, dosage for one day based on oral administration to an adult (60 kg) is about 1 mg to 1,000 mg, preferable about 10 mg to 750 mg, dosage for one day based on injection administration is about 0.3 mg to 200 mg, and the dosage may be administered once or may be divided into several times per day.

Effects of the Invention

According to the present invention, (tetrahydropyran-4-yl)-[2-phenyl-5-(1,1-dioxo-thiomorpholin-4-yl)methyl-1H-indol-7-yl]amine or a pharmaceutically acceptable salt thereof may effectively inhibit the fatty liver, inflammation and fibrosis of the liver, and may be used appropriately in the prevention or treatment of NAFLD, specifically NASH.

BRIEF DESCRIPTION OF DRAWINGS

The patent or application file contains at least one color drawing. Copies of this patent or patent application publication with color drawing will be provided by the USPTO upon request and payment of the necessary fee.

DESCRIPTION OF THE INVENTION

Hereinafter, the present invention is explained in more detail with the following examples. However, the following examples are only intended to facilitate understanding of the present invention, and the protection scope of the present invention is not limited thereto.

Example 1: Inhibitory Effect of (tetrahydropyran-4-yl)-[2-phenyl-5-(1,1-dioxo-thiomorpholin-4-yl)methyl-1H-indol-7-yl]amine on Fatty Liver (Evaluation Using Fatty Liver Model Accompanied by Obesity)

As experimental animals, 6-week-old male ob/+ mouse for control, and 6-week-old C57BL/6J Lep(−/−) male (ob/ob) mice were purchased from Harlan (Indianapolis, Ind.). The purchased mice were maintained under standard condition (25° C., 55% humidity and 12-hour light periodicity) with normal chow diet. 30 mice were divided into 3 groups, 10 mice in each group. Group 1 included 10 C57BL/6J(ob/+ control group) mice, Group 2 was vehicle-treated 10 ob/ob mice treated with saline solution, and Group 3 was a group in which (tetrahydropyran-4-yl)-[2-phenyl-5-(1,1-dioxo-thiomorpholin-4-yl)methyl-1H-indol-7-yl]amine (LG Life Sciences Ltd., Daejeon, Republic of Korea) was treated once a day by 20 mg/kg dosage. Saline solution and (tetrahydropyran-4-yl)-[2-phenyl-5-(1,1-dioxo-thiomorpholin-4-yl)methyl-1H-indol-7-yl]amine solution were orally administered for 4 weeks. After treatment, animals were anesthetized and sacrificed, and livers were rapidly taken and stored for the next analysis.

Example 1-1: Effect of (tetrahydropyran-4-yl)-[2-phenyl-5-(1,1-dioxo-thiomorpholin-4-yl)methyl-1H-indol-7-yl]amine on the TG Accumulation in Liver Cells, Cholesterol Accumulation, and Liver Damage in the Obese Fatty Liver Model FIG. 1 is a picture and graph showing the effect on decreasing the content of TG and cholesterol in ob/ob mouse when the compound (20 mg/kg/day) of the present invention is administered (n=10, p<0.001 vs vehicle).

Figure 1:
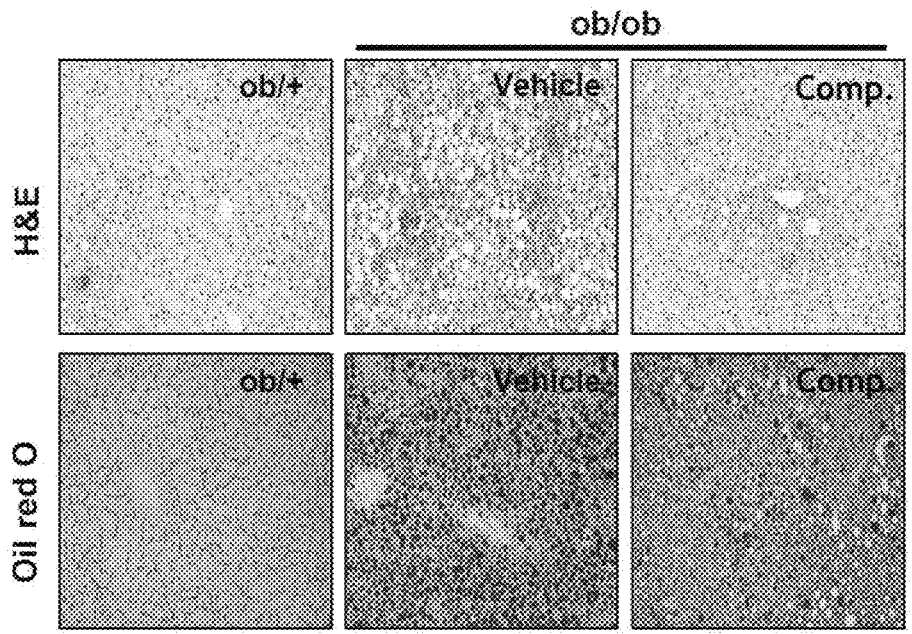
FIG. 1 is a picture and graph showing the effect of decreasing the content of TG and cholesterol in ob/ob mouse when the compound (20 mg/kg/day) of the present invention is administered (n=10, p<0.001 vs. vehicle).
Figure 1:
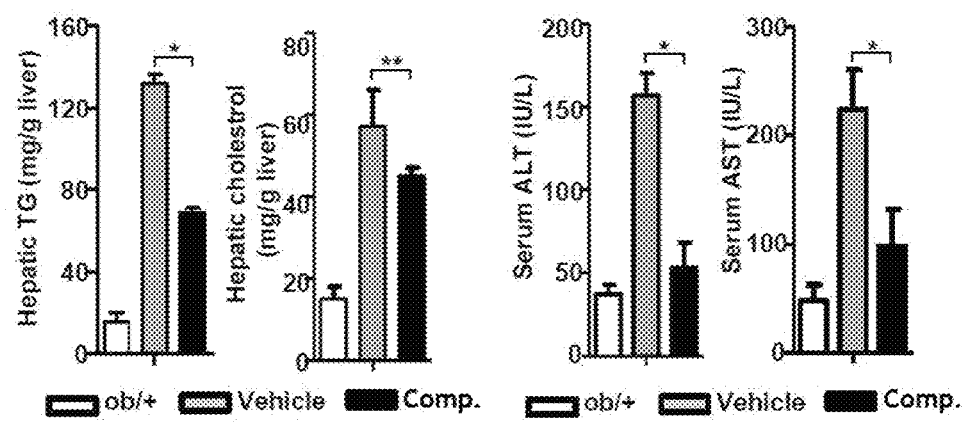

As shown in FIG. 1, when compared with the liver in the control group mice (ob/+), it was confirmed that ob/ob obese mice had an accumulation of approximately 60% of fatty tissue and lipid droplets of various sizes from small to big in the liver cells. Contrary to this, it was observed that in the case of obese mice which had oral administration of (tetrahydropyran-4-yl)-[2-phenyl-5-(1,1-dioxo-thiomorpholin-4-yl)methyl-1H-indol-7-yl]amine (Comp.) in dosage of 20 mg/kg once a day, when examined by the H&E staining method, the fatty tissue was remarkably decreased. In addition, compared to that of the vehicle-treated group, the Oil-Red O stained area was remarkably decreased in the case of (tetrahydropyran-4-yl)-[2-phenyl-5-(1,1-dioxo-thiomorpholin-4-yl)methyl-1H-indol-7-yl]amine-treated mice.

The TG level in the blood serum did not show much difference between the level of each group (data not shown), but the amount of liver TG and cholesterol showed a significant decrease in the group treated with the compound of the present invention. It was confirmed that the group treated with the compound of the present invention showed decreased ALT and AST value in blood serum, as compared with the group treated with vehicle.

Example 1-2: Evaluation of Effect of (tetrahydropyran-4-yl)-[2-phenyl-5-(1,1-dioxo-thiomorpholin-4-yl)methyl-1H-indol-7-yl]amine on Oxidative Stress and Lipid Oxidation in the Obese Fatty Liver Model FIG. 2 is a picture and a graph showing the effect on oxidative stress and lipid oxidation inhibition in ob/ob mouse when the compound (20 mg/kg/day) of the present invention is administered.

Figure 2:
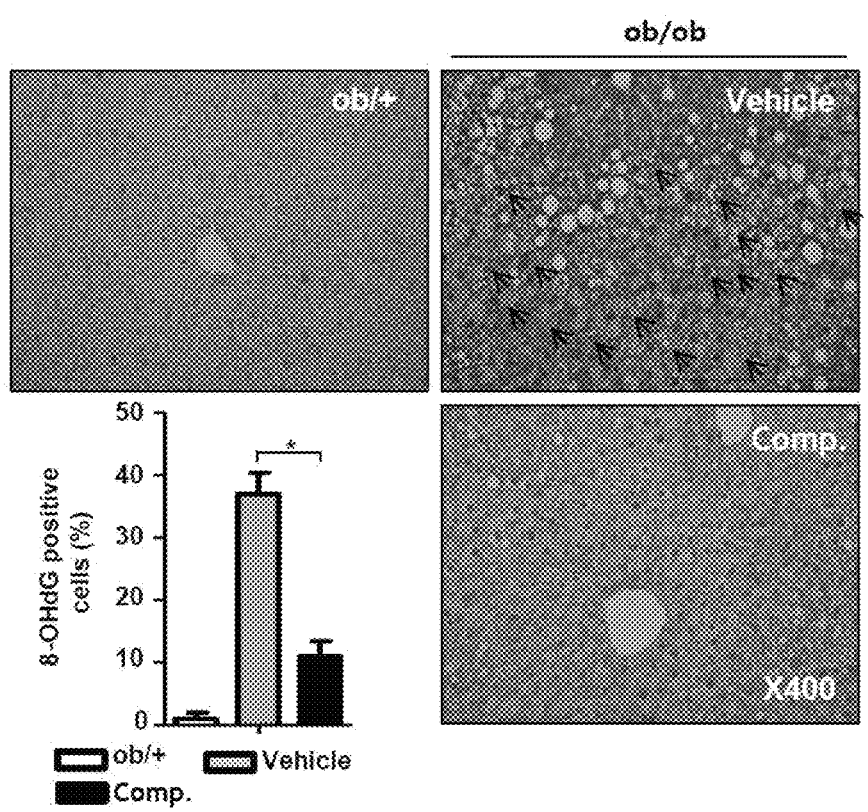
FIG. 2 is a picture and graph showing the effect on inhibiting oxidative stress and lipid oxidation in ob/ob mouse when the compound (20 mg/kg/day) of the present invention is administered.
Figure 2:
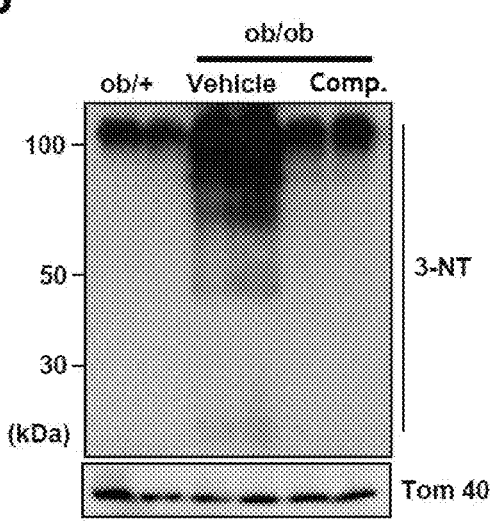
Figure 2:
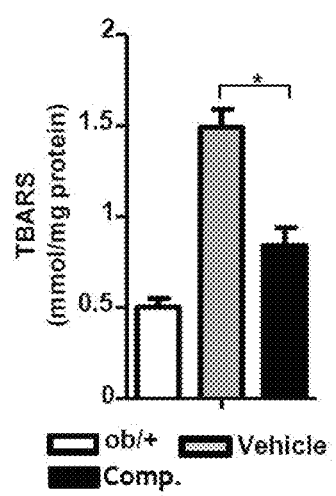

As shown in FIG. 2, the amount of 8-OHdG, which represents the DNA damage by oxidative stress, showed significant correlationship with the amount of ALT, and in the case of ob/ob mice treated with the compound of the present invention, the number of 8-OHdG positive liver cells were remarkably low as compared with that of the group treated with vehicle. In addition, the level of 3-NT (nitrotyrosine), which plays an important role in the disorder of mitochondrial function, was quite increased in the ob/ob mice, but considerably decreased in the group treated with (tetrahydropyran-4-yl)-[2-phenyl-5-(1,1-dioxo-thiomorpholin-4-yl)methyl-1H-indol-7-yl]amine. Moreover, in order to determine the effect of oxidative stress which is known as an important factor in the occurrence of NASH, the amount of TBARS was measured, and a significant decrease was observed when treated with (tetrahydropyran-4-yl)-[2-phenyl-5-(1,1-dioxo-thiomorpholin-4-yl)methyl-1H-indol-7-yl]amine.

In other words, the results shown in FIG. 2 reveal that (tetrahydropyran-4-yl)-[2-phenyl-5-(1,1-dioxo-thiomorpholin-4-yl)methyl-1H-indol-7-yl]amine according to the present invention has an effect of effectively inhibiting oxidative stress and nitration of proteins.

Example 1-3: Evaluation of Effect of (tetrahydropyran-4-yl)-[2-phenyl-5-(1,1-dioxo-thiomorpholin-4-yl)methyl-1H-indol-7-yl]amine on Mitochondrial Respiratory Chain Complex Based on the previous results in which (tetrahydropyran-4-yl)-[2-phenyl-5-(1,1-dioxo-thiomorpholin-4-yl)methyl-1H-indol-7-yl]amine inhibited ROS formation of mitochondria and oxidative damage by ROS, and effects of (tetrahydropyran-4-yl)-[2-phenyl-5-(1,1-dioxo-thiomorpholin-4-yl)methyl-1H-indol-7-yl]amine on the expression of mitochondrial respiratory chain complex and OXPHOS complex were evaluated in the liver of ob/ob mice treated with vehicle and (tetrahydropyran-4-yl)-[2-phenyl-5-(1,1-dioxo-thiomorpholin-4-yl)methyl-1H-indol-7-yl]amine FIG. 3 is a picture and a graph showing the effect on enhancing the activation of the reduced respiratory chain of mitochondria in ob/ob mouse when the compound (20 mg/kg/day) of the present invention is administered.

As shown in FIG. 3A, the expression of liver mitochondrial complex I, III, IV and V in the ob/ob mice was remarkably decreased as compared with ob/+ control group. However, in the case of ob/ob mice treated with the compound of the present invention, the expression of those mitochondrial complexes was remained up to the level of the control group. In addition, the results of examination of OXPHOS complex by BN-PAGE, OXPHOS complexes I, III, IV and V were remarkably decreased, as compared with the ob/+ control group. However, in the case of ob/ob mice treated with (tetrahydropyran-4-yl)-[2-phenyl-5-(1,1-dioxo-thiomorpholin-4-yl)methyl-1H-indol-7-yl]amine for 4 weeks, it was shown that the binding between the complexes were enhanced. Characteristically, in the case of treatment with (tetrahydropyran-4-yl)-[2-phenyl-5-(1,1-dioxo-thiomorpholin-4-yl)methyl-1H-indol-7-yl]amine, the activation of the mitochondrial respiration chain complexes I, III, IV and V was meaningfully increased, while the activation of complex IT did not show much difference.

Figure 3:
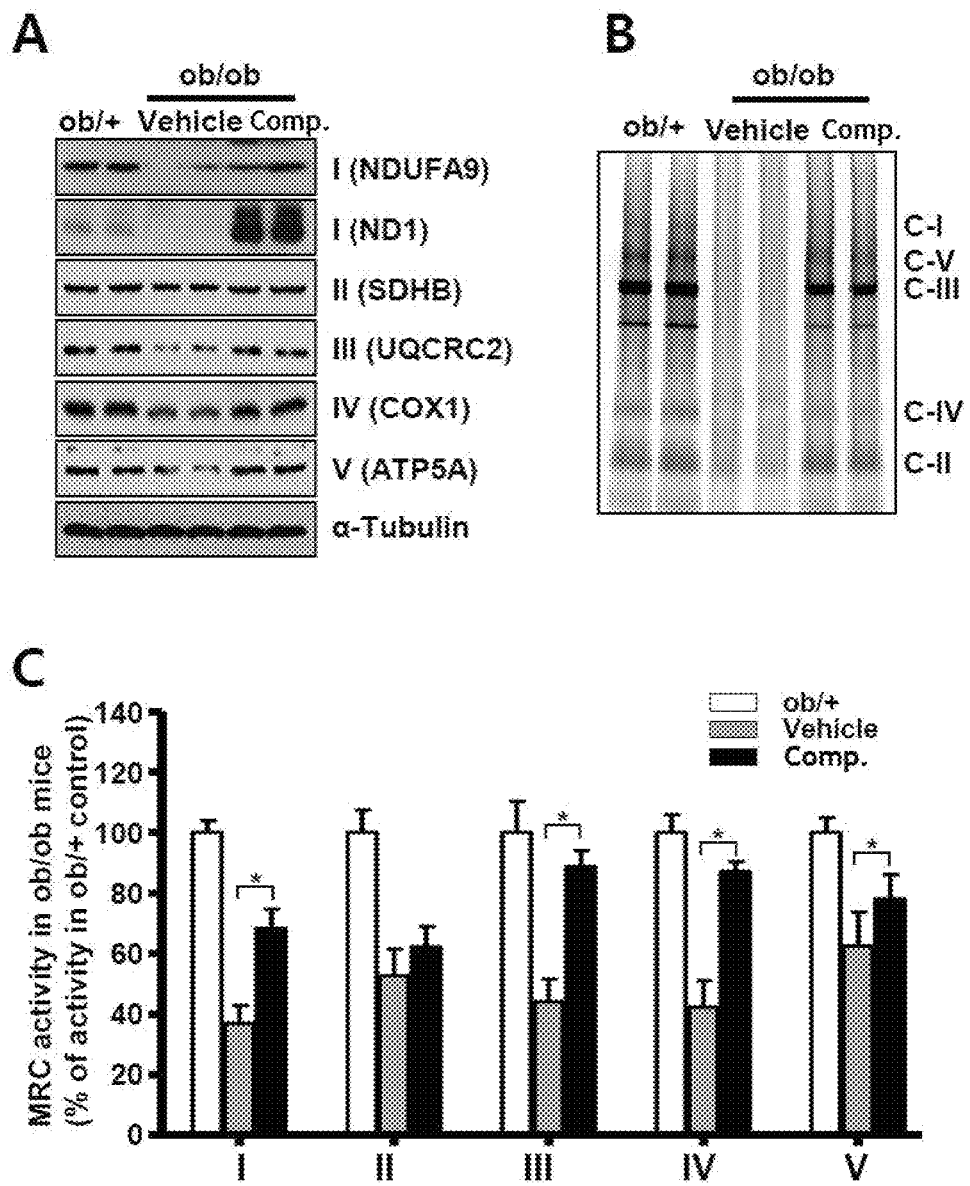
FIG. 3 is a picture and graph showing the effect on enhancing the activation of the reduced respiratory chain of mitochondria in ob/ob mouse when the compound (20 mg/kg/day) of the present invention is administered.

In other words, results shown in FIG. 3 suggests that (tetrahydropyran-4-yl)-[2-phenyl-5-(1,1-dioxo-thiomorpholin-4-yl)methyl-1H-indol-7-yl]amine according to the present invention improves mitochondrial respiration chain activation and mitochondria activation.

Example 1-4: Evaluation of Effect of (tetrahydropyran-4-yl)-[2-phenyl-5-(1,1-dioxo-thiomorpholin-4-yl)methyl-1H-indol-7-yl]amine on Inflammatory Cytokines and Macrophage (Kupffer Cell) in ob/ob Mice Liver Inflammation and oxidative stress are known as key factors in the occurrence and development of NAFLD and NASH. The present inventors analyzed the phosphorylation of NF-κB, p38 and JNK 1/2 related to the inflammatory signal by the use of immunoblotting.

Figure 4:
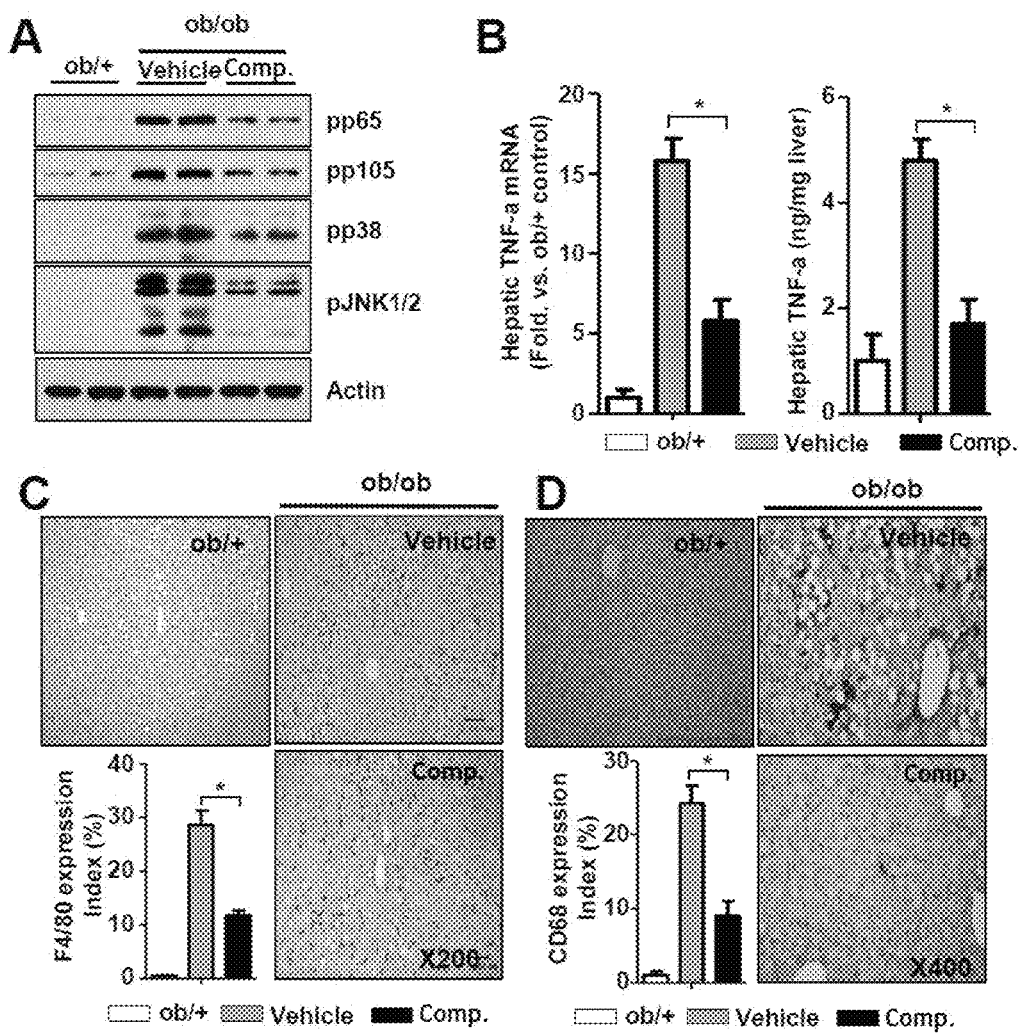
FIG. 4 is a picture and graph showing the effect on decreasing the increased expression of inflammatory cytokines and the activation of macrophagocyte in ob/ob mouse when the compound (20 mg/kg/day) of the present invention is administered.

FIG. 4 is a picture and graph showing the effect on decreasing the increased expression of inflammatory cytokines and the activation of macrophage in ob/ob mouse when the compound (20 mg/kg/day) of the present invention is administered.

As shown in FIG. 4A, in the liver of ob/ob mice treated with vehicle, the expression of phosphorylated NF-κB, p65 and p105 was increased, and the level of phosphorylation of p38 and JNK 1/2, which are inflammation markers, was increased. Contrary to this, in the case of ob/ob mice treated with the compound of the present invention, the phosphorylation of NF-κB p65. NF-κB p105, p38 and JNK 1/2 was significantly decreased. These results show that (tetrahydropyran-4-yl)-[2-phenyl-5-(1,1-dioxo-thiomorpholin-4-yl)methyl-1H-indol-7-yl]amine effectively inhibits the signaling cascade related to inflammation which is the important mechanism in the occurrence of NAFLD.

In addition, while ob/ob mice treated with vehicle showed notable increase of the expression of mRNA of TNF-α in the liver, the expression of TNF-α was inhibited in mice treated with (tetrahydropyran-4-yl)-[2-phenyl-5-(1,1-dioxo-thiomorpholin-4-yl)methyl-1H-indol-7-yl]amine. As a result of ELISA analysis with samples collected from the minced liver, in the case of mice treated with (tetrahydropyran-4-yl)-[2-phenyl-5-(1,1-dioxo-thiomorpholin-4-yl)methyl-1H-indol-7-yl]amine, a significantly low amount of TNF-alpha was shown (FIG. 4B).

Interestingly, no difference of the amount of IL-6 mRNA was shown between the group treated with vehicle and the group treated with the compound of the present invention. In addition, as a result of immune staining of F4/80 (FIG. 4C) and Cd68 (FIG. 4D), infiltration of many activated macrophages was observed in the liver of ob/ob mice treated with vehicle, but in the case of treatment with (tetrahydropyran-4-yl)-[2-phenyl-5-(1,1-dioxo-thiomorpholin-4-yl)methyl-1H-indol-7-yl]amine, it was shown that the inflammation reaction was decreased.

Example 2: Inhibitory Effect of (tetrahydropyran-4-yl)-[2-phenyl-5-(1,1-dioxo-thiomorpholin-4-yl)methyl-1H-indol-7-yl]amine on Inflammation and Fibrosis of Liver (Evaluation Using Steatohepatitis Model which Accompanies Obesity)

In order to determine the level of liver fibrosis, trichrome staining and the expression of collagen I was measured and analyzed.

Figure 5:
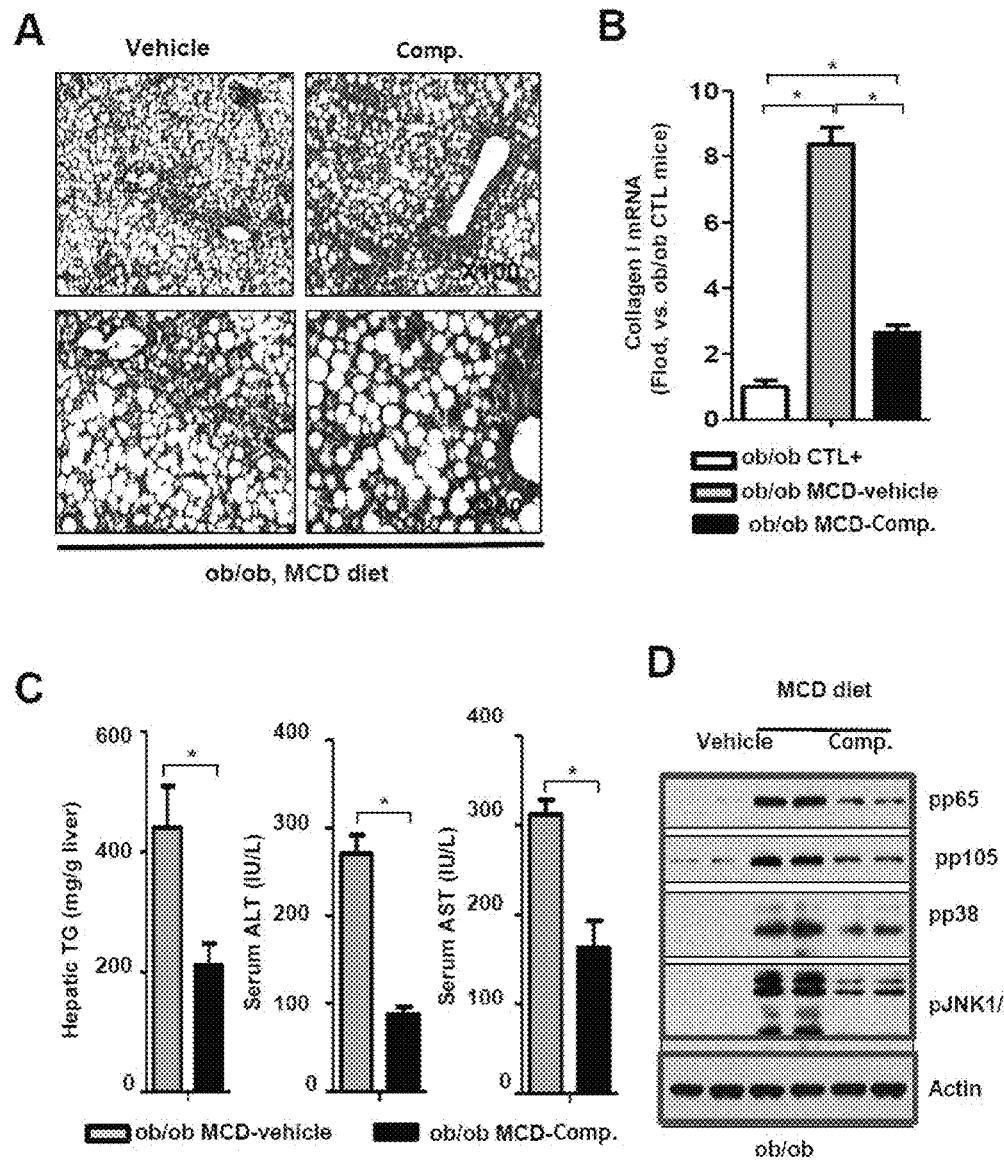
FIG. 5 is a picture and graph showing the effect on inhibiting liver fibrosis in ob/ob mouse with MCD (methionine choline-deficient) diet when the compound (20 mg/kg/day) of the present invention is administered.

FIG. 5 is a picture and graph showing the effect of inhibiting liver fibrosis in ob/ob mouse with MCD (methionine choline-deficient) diet when the compound (20 mg/kg/day) of the present invention is administered.

As shown in FIGS. 5A and 5B, it was confirmed that in the case of a MCD diet deficient in methionine and choline, much influence was shown in progress of liver fibrosis in ob/ob mice. On the other hand, (tetrahydropyran-4-yl)-[2-phenyl-5-(1,1-dioxo-thiomorpholin-4-yl)methyl-1H-indol-7-yl]amine-treated group showed inhibited intensity of trichrome staining and expression of collagen I when compared to vehicle-treated group.

As shown in the FIG. 5C, ob/ob mice with MCD diet contain much more liver TG compared to ob/ob mice with normal diet. However, liver TG amount of (tetrahydropyran-4-yl)-[2-phenyl-5-(1,1-dioxo-thiomorpholin-4-yl)methyl-1H-indol-7-yl]amine-treatment group showed about 50% decrease (ob/ob MCD-vehicle 400+/−80 mg/g liver, ob/ob MCD-Comp 210+/−20). In addition, the amount of ALT and AST in blood serum was remarkably decreased in the group treated with the compound of the present invention.

Furthermore, FIG. 5D showed that the phosphorylation of NF-γB p65, NF-κB p105, p38 and JNK 1/2 was increased considerably in ob/ob mice with MCD diet, when compared to ob/ob mice with normal diet. On the other hand, it was shown that the phosphorylation of fibrosis markers was inhibited by the treatment with the compound of the present invention.

Such test results imply that inflammation signal and liver fibrosis is notably increased in ob/ob mice with MCD diet, but the compound of the present invention can be used as a potential medicament for treatment by effectively blocking the progress to liver fibrosis, thereby improving the function of the liver.

As explained above, it is confirmed that (tetrahydropyran-4-yl)-[2-phenyl-5-(1,1-dioxo-thiomorpholin-4-yl)methyl-1H-indol-7-yl]amine according to the present invention inhibits TG accumulation, cholesterol accumulation and liver damage in the obese fatty liver model, blocks oxidative stress and lipid oxidation, enhances mitochondrial respiration chain activation and mitochondria activation, inhibits activation of inflammatory cytokines and macrophage (Kupffer cell), and it has efficacy of inhibiting inflammation and fibrosis of the liver in steatohepatitis model accompanying obesity. Accordingly, (tetrahydropyran-4-yl)-[2-phenyl-5-(1,1-dioxo-thiomorpholin-4-yl)methyl-1H-indol-7-yl]amine or a pharmaceutically acceptable salt thereof according to the present invention can effectively inhibit fatty liver, inflammation and fibrosis of the liver, and is expected to be used suitably to prevent or treat NAFLD, specifically NASH.

The invention claimed is:
1. A method for the treatment of non-alcoholic steatohepatitis which comprises administering (tetrahydropyran-4-yl)-[2-phenyl-5-(1,1-dioxo-thiomorpholin-4-yl)methyl-1H-indol-7-yl]amine or a pharmaceutically acceptable salt thereof to a subject in need thereof, wherein the non-alcoholic steatohepatitis is caused by accumulation of liver fat, and oxidative stress or inflammatory cytokine derived from fatty liver.

2. The method according to the claim 1, wherein (tetrahydropyran-4-yl)-[2-phenyl-5-(1,1-dioxo-thiomorpholin-4-yl)methyl-1H-indol-7-yl]amine or a pharmaceutically acceptable salt thereof inhibits accumulation of liver fat, and inflammation and fibrosis of liver by inhibiting oxidative stress or inflammatory cytokine derived from fatty liver.

* * * * *